United States Patent [19]
Nilsson

[11] Patent Number: 5,873,851
[45] Date of Patent: Feb. 23, 1999

[54] OPHTHALMIC IRRIGATOR-ASPIRATOR HAVING A FLEXIBLE OUTER CANNULA

[75] Inventor: Isidro G. Nilsson, Marysville, Wash.

[73] Assignee: MicroSurgical Technology, Inc., Redmond, Wash.

[21] Appl. No.: 705,898

[22] Filed: Aug. 28, 1996

[51] Int. Cl.$^6$ .................................................. A61M 3/00
[52] U.S. Cl. .......................... 604/43; 604/22; 604/274; 606/107
[58] Field of Search ................................ 604/27, 35, 43, 604/274, 282, 294, 22, 44; 606/107

[56] References Cited

U.S. PATENT DOCUMENTS

| 3,605,725 | 9/1971 | Bentov | 604/280 |
|---|---|---|---|
| 4,364,394 | 12/1982 | Wilkinson | 604/35 |
| 4,578,059 | 3/1986 | Fabricant et al. | 604/43 |
| 4,652,255 | 3/1987 | Martinez | 604/27 |
| 4,790,812 | 12/1988 | Hawkins, Jr. et al. | 604/27 |
| 4,897,079 | 1/1990 | Zaleski et al. | 604/43 |
| 5,024,654 | 6/1991 | Tyler | 604/43 |
| 5,300,022 | 4/1994 | Klapper et al. | 604/35 |
| 5,603,703 | 2/1997 | Elsberry et al. | 604/274 |
| 5,656,029 | 8/1997 | Imran et al. | 604/95 |
| 5,685,841 | 11/1997 | Mackool | 604/35 |
| 5,741,226 | 4/1998 | Strukel et al. | |

Primary Examiner—Mark Bockelman
Attorney, Agent, or Firm—Christensen O'Connor Johnson & Kindness PLLC

[57] ABSTRACT

The outer cannula of an ophthalmic irrigator-aspirator has rigid tip and butt sections and a more flexible central section. The central section can be an elastomeric sleeve that extends between the tip and butt sections. The outer cannula includes reinforcement members that prevent the elastomeric sleeve from becoming completely closed by compression caused by a tight fit in an incision in a patient's cornea. The reinforcement members may be rigid or somewhat flexible.

4 Claims, 5 Drawing Sheets

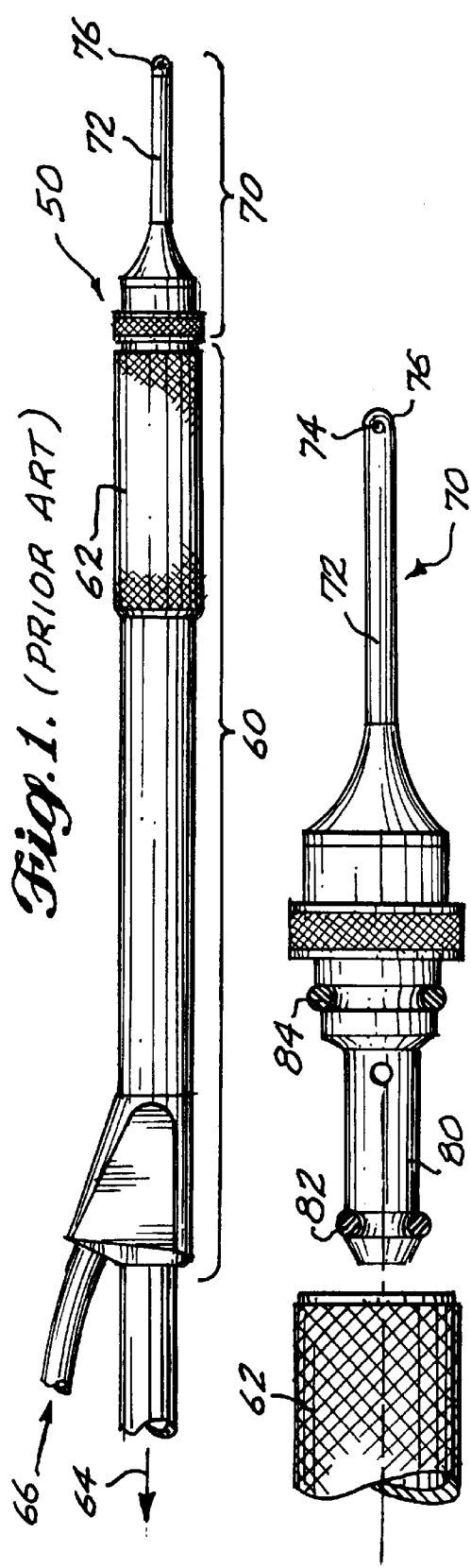
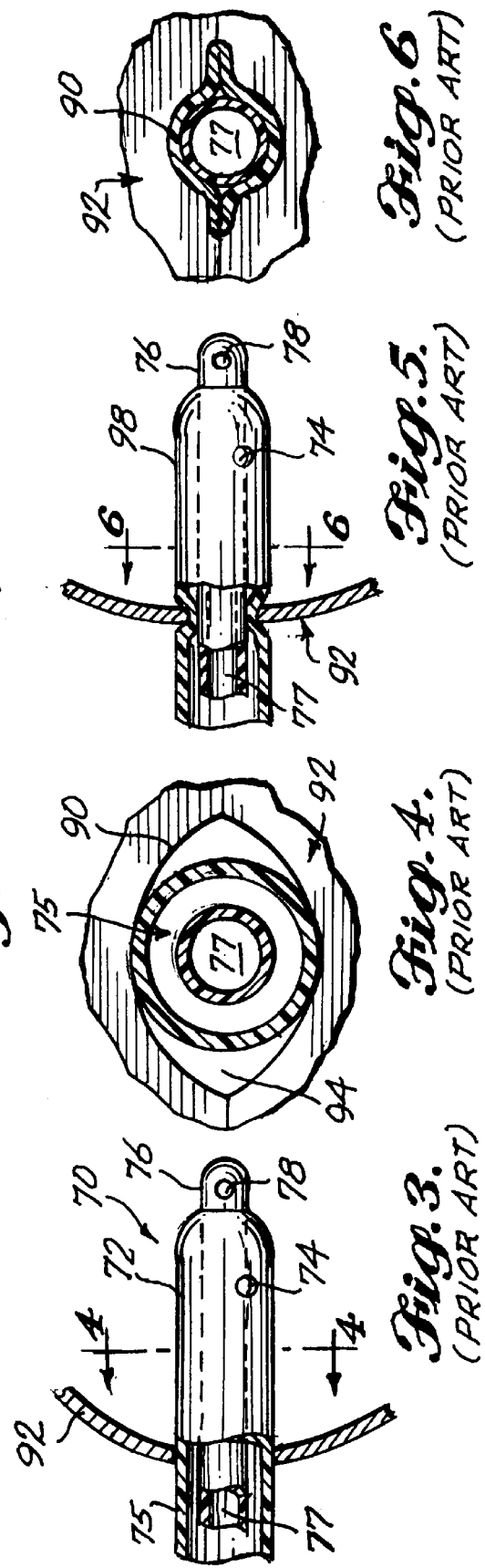

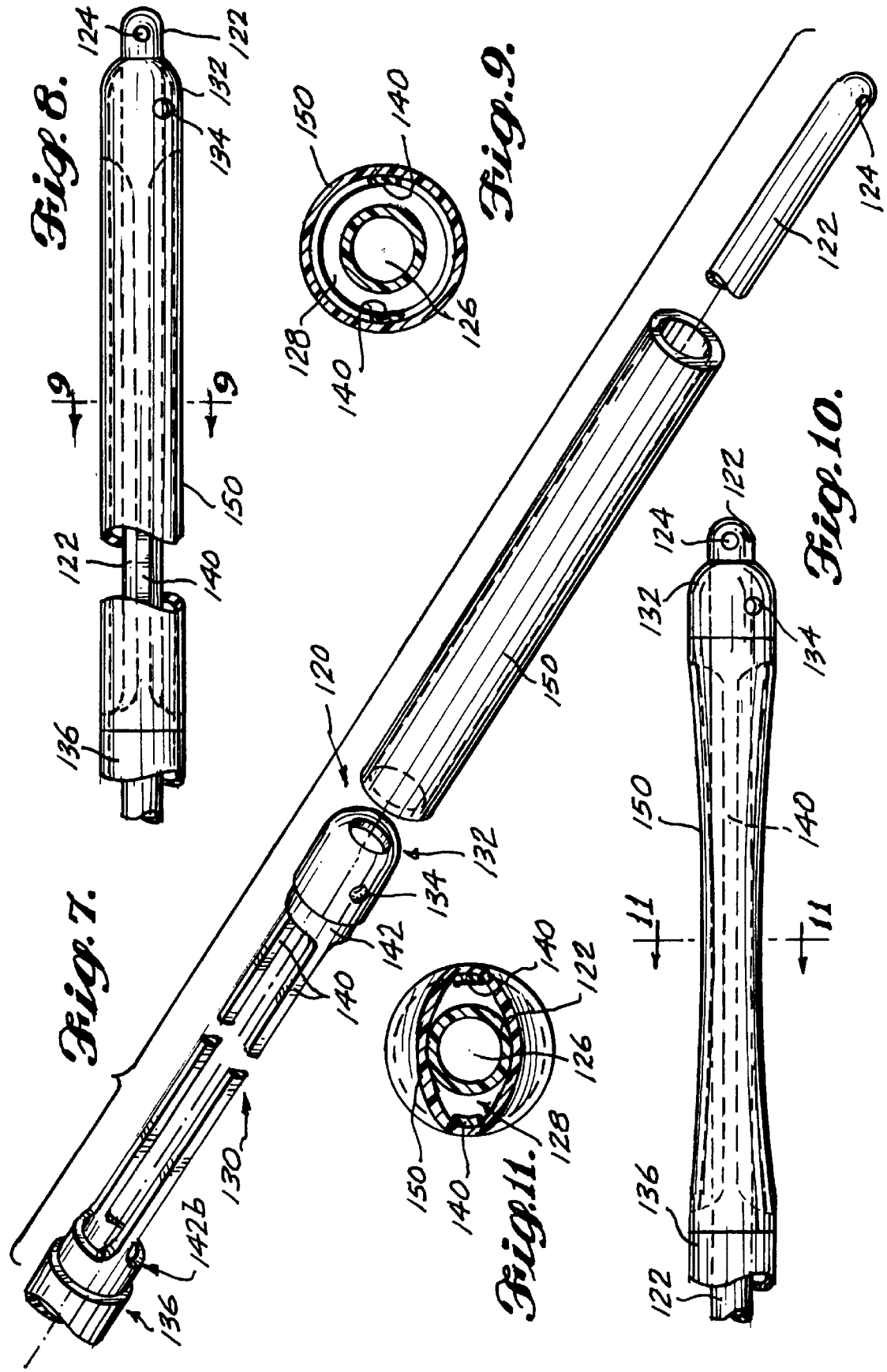

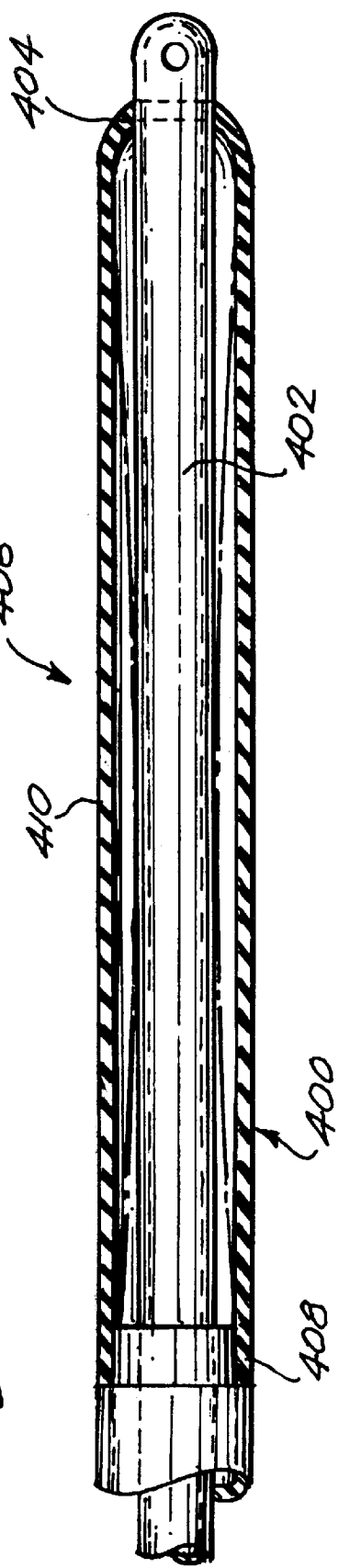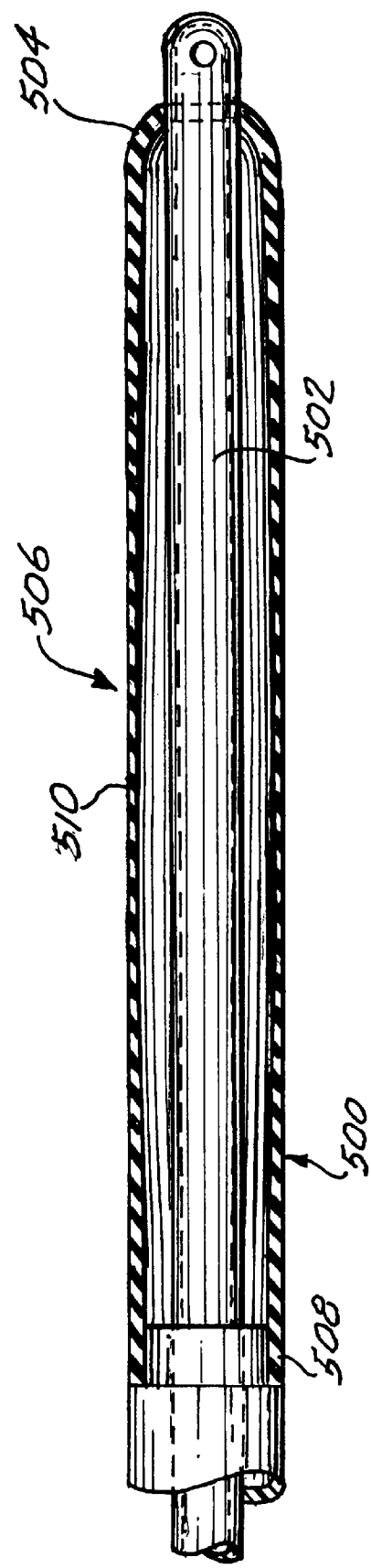

OPHTHALMIC IRRIGATOR-ASPIRATOR HAVING A FLEXIBLE OUTER CANNULA

FIELD OF THE INVENTION

The present invention relates generally to surgical devices, and in particular to phacoemulsifiers and irrigation-aspiration tools for removing phaco-emulsified lenses and cleaning the lens capsule.

BACKGROUND OF THE INVENTION

One of the more common afflictions to affect aging eyes are cataracts, which cause gradually deteriorating vision. Advances in ophthalmic surgery allow many cataracts to be removed and vision restored.

Treating cataracts typically involves the removal of the clouded natural lens and replacement with an artificial lens. Removal of the lens requires an incision or tunnel to be made in and/or adjacent to the cornea and a phaco-emulsifier to be inserted into the eye. The phaco-emulsifier vibrates ultrasonically to liquify the lens. The emulsified lens is removed from the eye via aspiration and the artificial lens is then inserted. Modern phacoemulsifiers and aspirators have small cylindrical tips with coaxial passages, one for irrigation and the other for aspiration.

It is desirable that the incision or tunnel be as small as possible. Nevertheless, one potential problem with the emulsification and aspiration procedure is damage to the cornea when the tip of a phacoemulsifier or aspirator is inserted through the incision and/or is manipulated within the lens capsule. The tip can tear the incision slightly and complicate the healing process. In addition, a conventional tip does not always create a good seal with the incision, thereby leading to increased fluid loss.

One approach toward a solution to these problems is to provide a resilient sleeve around a rigid inner cannula. However, pressure at the corneal incision can crimp the sleeve and hinder effective irrigation and aspiration.

SUMMARY OF THE INVENTION

The present invention provides an improved ophthalmic irrigation-aspiration tip for a phacoemulsifier or an aspirator. The improved tip includes a rigid or flexible inner cannula, and an outer cannula having a rigid tip but a resilient central portion. In one embodiment the resilient central portion is an elastomeric sleeve. Reinforcing members run along the sleeve to allow the sleeve to be deformed by the incision but prevent the sleeve from being pinched closed. The reinforcing members can be fashioned in a variety of forms, including widely spaced rigid ribs, more closely spaced flexible wires or a flexible spring. The reinforcing members can be integral with the outer cannula or can be embedded within the elastomeric sleeve. In an alternative embodiment, the rigid tip and resilient central section can be integral, such as by changing the blend of polymers during extrusion.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a side elevation of a conventional ophthalmic irrigation-aspiration tool;

FIG. 2 is an enlarged side elevation of the tip section of the tool of FIG. 1;

FIG. 3 is a further enlarged, diagrammatic side elevation illustrating insertion of the irrigation-aspiration tip of FIG. 1 through a cornea;

FIG. 4 is a further enlarged section along line 4—4 of FIG. 3 showing how the conventional irritation-aspiration tip fits within an incision made in the cornea;

FIG. 5 is a side elevation corresponding to FIG. 3 illustrating insertion of another prior art irrigation-aspiration tip through a cornea;

FIG. 6 is a section along line 6—6 of FIG. 5 showing how the outer cannula of the irrigation-aspiration tip of FIG. 5 can be pinched closed at an incision;

FIG. 7 is a top front perspective of an irrigation-aspiration tip according to the present invention, with parts shown in exploded relationship;

FIG. 8 is a side elevation of the irrigation-aspiration tip of FIG. 7, with parts assembled and with some parts broken away;

FIG. 9 is a section along line 9—9 of FIG. 8;

FIG. 10 is a side elevation corresponding to FIG. 8 but with the irrigation-aspiration tip in a compressed state;

FIG. 11 is a section along line 11—11 of FIG. 10;

FIGS. 15 and 16 are perspectives of other embodiments of the irrigation-aspiration tip in accordance with the present invention

DETAILED DESCRIPTION OF THE PREFERRED EMBODIMENT

Figure 12:
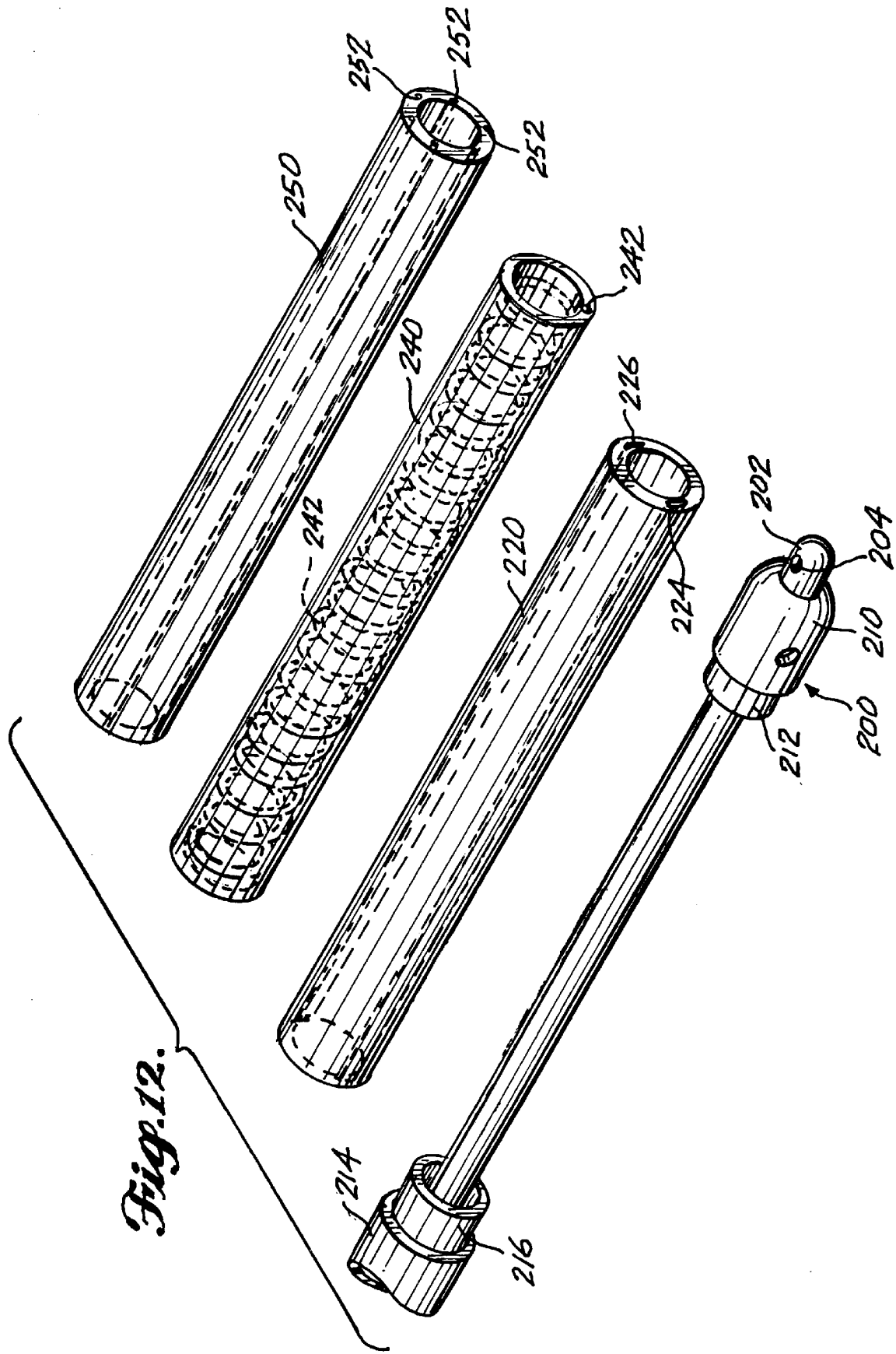
FIG. 12 is a perspective illustrating alternative embodiments of an irrigation-aspiration tip in accordance with the present invention.

As described above, the most common treatment for cataracts is to emulsify the clouded natural lens, aspirate the lens from the eye and replace the lens with an artificial lens. A phacoemulsifying tool achieves a first stage of aspiration and then is removed from the corneal incision. An irrigation-aspiration tool of the type shown in FIG. 1 is inserted. As used herein, the term "aspirator" includes the phacoemulsifier and the separate irrigation-aspiration tool.

The conventional aspirator 50 shown in FIG. 1 includes a handle section 60 that is held by the surgeon and a tip section 70 that is inserted through the cornea. The tip section of the aspirator has two passages. An inner axial passage through an inner cannula 76 is used to aspirate the emulsified lens. An outer passage through an outer cannula 72 delivers a stream of saline solution 64 into the eye. The simultaneous injection of saline solution into the eye while the emulsified lens is being aspirated prevents the lens capsule from collapsing. After the emulsified lens has been aspirated, the surgeon removes the aspirator and inserts an artificial lens according to techniques that are well known in the art.

FIG. 2 is a more detailed view of the tip section 70 of the conventional aspirator. The tip 70 includes a barrel section 80 that is received within the handle 60 thereby allowing the same handle to be used with multiple interchangeable tips. The tip, surrounding and coaxial with the first, is sealed within the handle by a pair of O-rings 82, 84 that seat within corresponding races (not shown) to isolate the inner and outer passages.

As described above, one problem with a conventional aspiration tip of the type shown in FIGS. 1 and 2 is that it can damage the cornea when inserted and/or when manipulated to remove the emulsified lens. FIG. 3 and FIG. 4 show how the tip is inserted through a patient's cornea 92. Saline solution is delivered through a passage or bore 75 that is formed between the inner cannula 76 and the outer cannula 72, and exits through a port 74. The emulsified lens is aspirated through a port 78, into the inner passage or bore 77 of the inner cannula.

As best seen in FIG. 4, a conventional outer cannula creates gaps 94 at the ends of the incision that contribute to excess fluid loss from the eye during the irrigation-aspiration procedure. In addition, the rigid outer cannula can stretch the cornea and cause the incision to tear as the tip is inserted or moved within the lens capsule.

One prior attempt to solve the problem created by rigid aspirator tips is to make the outer cannula of a readily deformable material. FIG. 5 shows an aspiration tip with an outer cannula 98 of soft silicon rubber material. While the soft silicon rubber cannula helps avoid tearing the incision and seals the incision to prevent fluid loss, the force of the incision on the soft outer cannula can cause it to collapse or pinch, thereby inhibiting the flow of the saline solution, as can be seen in FIG. 6.

To solve the problems associated with the prior art, the present invention utilizes a tip that is only partially deformable. As shown in FIG. 7, the tip 120 of the present invention preferably includes a rigid or flexible inner cannula 122 having an aspiration port 124 at its distal end for aspirating cortical material from the eye. An outer cannula 130 is concentrically disposed over the inner cannula.

The outer cannula 130 includes a rigid tip section 132 and a rigid butt section 136. The tip section has a port 134 at its distal end to inject saline solution into the eye. Separating the tip section and the butt section along the length of the inner cannula are reinforcing members comprising a pair of diametrically opposed, relatively rigid ribs 140. Each of the ribs joins the respective tip and butt section at shoulders 142a, 142b having slightly smaller diameters than the tip and butt sections. The outer cannula 130 fits over the inner cannula 122 and is secured in position conventionally, such as by brazing. To complete the tip, an elastomeric sleeve 150 is slid over the outer cannula to seat between the shoulder sections 142a and 142b. When seated, the elastomeric sleeve has an outer diameter substantially equal to the outer diameters of the tip and butt sections, as can be seen in FIG. 8.

FIG. 9 is a cross-sectional view of the aspirator tip 120. As can be seen, an inner passage or channel 126 is formed within the inner cannula 122 and an outer passage or channel 128 is formed between the inner cannula 122 and the outer elastomeric tube 150.

FIG. 10 shows how the elastomeric sleeve 150 can be radially compressed between the ribs 140 so that the central portion of the outer cannula has an upright dimension less than the upright dimensions of the rigid tip and butt sections. FIG. 11 shows a cross section of the outer cannula in a compressed state. The elastomeric sleeve 150 can be compressed between the ribs up to a point where the sleeve meets the inner cannula 122. However, the rigid ribs 140 prevent the complete compression of the elastomeric sleeve in order to maintain the outer channel open and prevent blockage. The aspirator tip shown in FIGS. 7–11 provides the advantage of reducing the likelihood of tearing the cornea during surgery while at the same time not being pinched to block the outer aspiration channel. In addition, the compression of the elastomeric sleeve creates a good seal with the incision to minimize fluid loss.

FIG. 12 shows alternative embodiments of the tip according to the present invention. The tip 200 includes an inner cannula 202 having an input port 204. An outer cannula includes a rigid tip section 210 and a butt section 214. In this embodiment, the tip and butt sections are independent of each other and are independently secured to the inner cannula. The tip section 210 includes a shoulder 212 and the butt section includes a shoulder 216 that are both directed to the open center section of the outer cannula. A flexible sleeve is slid over the tip section 210 to seat on the shoulders 212, 216 in order to complete the outer cannula. In this embodiment of the invention, the support members of the outer cannula are embedded in the flexible rubber tubing. A first embodiment of the elastomeric sleeve 220 has a pair of diametrally opposed rigid or substantially rigid ribs 224, 226 that are embedded in the tube and oriented along the length of the sleeve 220. When the sleeve 220 is seated, the ribs 224, 226 within the sleeve prevent the outer cannula from completely collapsing.

An alternative embodiment of the elastomeric sleeve is a sleeve 240 having an embedded reinforcing helical spring 242. The helical spring has a stiffness such that the elastomeric sleeve can be partially compressed in order to make a good seal when inserted through the incision in the cornea. However, the spring provides sufficient support that the outer cannula is not completely pinched closed at the incision.

A third embodiment is an elastomeric tube 250 that has multiple flexible reinforcing wires 252 embedded in the tube. The wires 252 are sufficiently stiff that they prevent the tube from collapsing under the force of the incision, yet are supple enough to allow the outer cannula to compress and form a good seal. In this embodiment, preferably several wires are used, spaced uniformly around the circumference of the tube.

Figure 13:
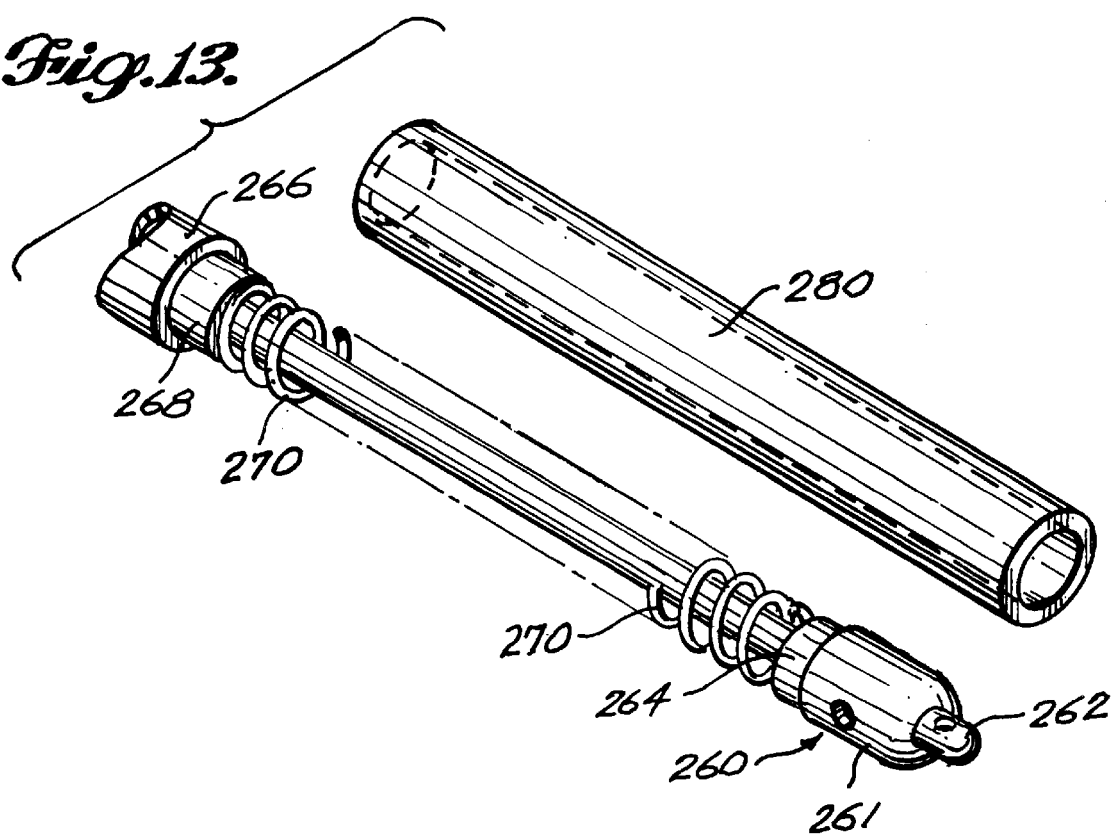
FIG. 13 is a perspective of another alternative embodiment of an irrigation-aspiration tip in accordance with the present invention.

FIG. 13 shows yet another embodiment of the invention whereby the tip 260 includes an inner cannula 262 and an outer cannula formed by a rigid tip section 261 and a rigid butt section 266. The tip section includes a shoulder 264 and the butt section includes a shoulder 268 that are directed toward the center section of the outer cannula. Secured between the shoulders 264, 268 is a helical spring 270. An elastomeric sleeve 280 is slid over the tip section 262 so that the outer periphery of the spring 270 abuts the inner periphery of the elastomeric tube. After surgery, the elastomeric tube 280 can be removed and the tip including the spring 270 can be sterilized.

Figure 14:
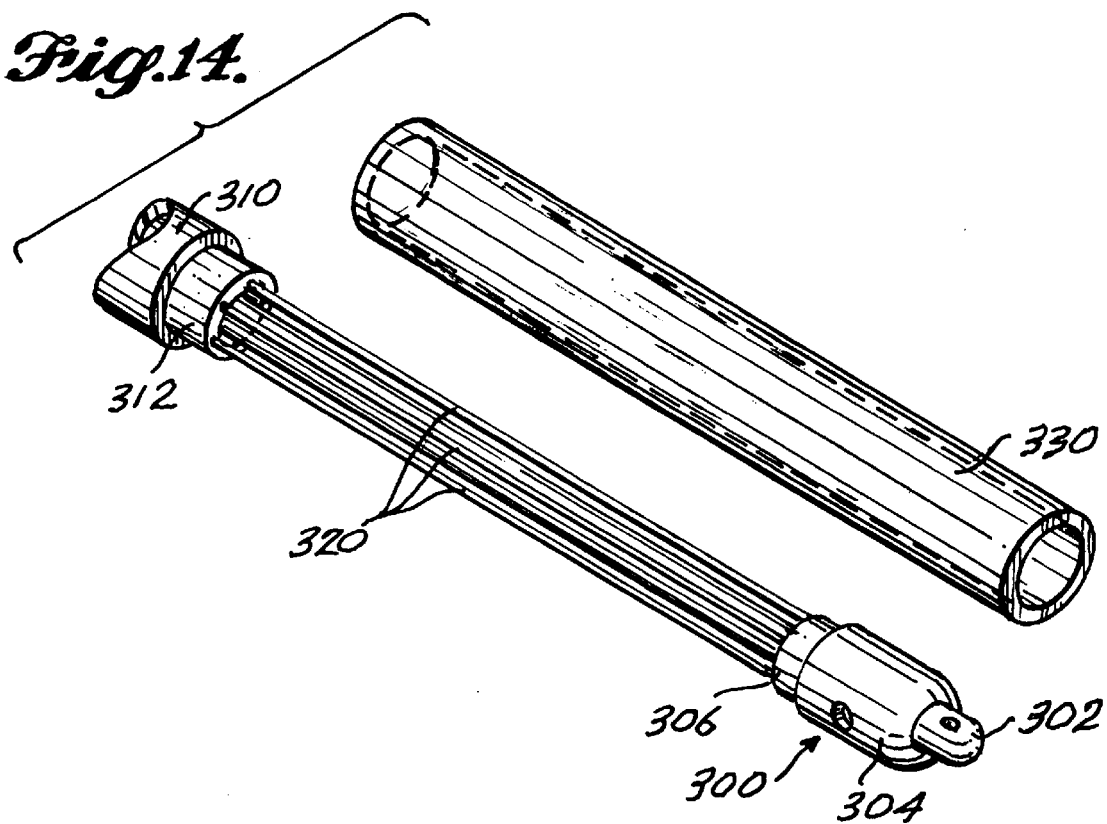
FIG. 14 is a perspective of yet another embodiment of an irrigation-aspiration tip in accordance with the present invention.

In the embodiment of the invention shown in FIG. 14, a tip 300 includes an inner cannula 302 and an outer cannula formed of a rigid tip section 304 and a rigid butt section 310. The tip section includes a shoulder 306 and the butt section includes a shoulder section 312. Secured between the shoulders 306, 312 are several flexible wires 320 that are equally spaced about the circumference of the outer cannula and extend between the shoulders 306, 312. Six such wires can be used. An elastomeric sleeve 330 can be slipped over the tip section 304 to seat on the shoulders 306, 312. The flexible wires 310 provide sufficient support that the outer cannula is not completely pinched closed by the force of the corneal incision, but do allow some compression to reduce potential damage to the eye and to provide a more effective seal.

In the embodiment of the present invention shown in FIG. 15, a tip 400 includes an inner cannula 402 and a unitary outer cannula 404. The outer cannula includes a rigid or at least stiff tip section 406 and, preferably a rigid or at least stiff butt section 408. The central section 410 extending between the tip and butt sections is more resilient, such that it can be partly compressed by the force of the corneal incision. In a unitary outer cannula having a central section integral with the tip and butt sections, this can be achieved by varying the polymer blend, such as during extrusion of the outer cannula. Another alternative, shown in FIG. 16, is to vary the wall thickness lengthwise of the outer cannula, while maintaining a uniform wall thickness for each cross section. The tip 506 and butt 508 of the outer cannula 504 thus are more rigid than the central portion 510 for this embodiment of aspirator 500. In either event, the stiffness of the tip section aids in precise placement and insertion of the aspirator tip, but the more flexible or resilient central section lessens the chance of tearing the corneal incision and provides a more effective seal as the tip is manipulated for aspiration of an emulsified lens.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A tip for an ophthalmic instrument for irrigation-aspiration at the interior of the cornea of an eye, comprising:

an inner cannula having a first port at its distal end for receiving or delivering a liquid;

an outer cannula disposed over the inner cannula and having a substantially rigid distal tip section of a diameter greater than the diameter of the inner cannula for insertion through a corneal incision, said rigid distal tip section of said outer cannula extending outward from the inner cannula and having a second port at the distal end for receiving or delivering a liquid at the interior of the cornea, said outer cannula having a body section, proximate to said tip section, having a rigidity less than the rigidity of the tip section and located for placement at the corneal incision for deformation at the corneal incision during use of the ophthalmic instrument with the rigid distal tip section located at the interior of the cornea, said body section being spaced outward from said inner cannula and being spaced proximally from the distal tip of the outer cannula, said outer cannula further comprising a butt section that is spaced from the tip section and joined thereto by one or more reinforcement members, and said body section comprising a sleeve of resilient material separate from said butt and tip sections and overlying said one or more reinforcement members between said butt and tip sections wherein said one or more reinforcement members provide support for said body section.

2. The tip of claim 1, wherein the support members include a pair of diametrally opposed rigid ribs extending between the butt section and tip sections of the outer cannula.

3. A tip for an irrigator-aspirator for the injection and removal of fluids through an incision in the cornea of an eye, comprising:

an inner cannula having a port disposed at a distal end;

an outer cannula including a rigid tip section, a butt section and support means joining the rigid tip and butt sections and a resilient sleeve overlying said support means between the rigid tip section and butt section, said support means permitting inward movement of the sleeve within the support means towards the inner cannula while for preventing the sleeve from becoming sealed against the inner cannula when the irrigator-aspirator is inserted through the incision.

4. The tip of claim 3, wherein the support means comprises a pair of ribs joining the butt section and the rigid tip section.

* * * * *

UNITED STATES PATENT AND TRADEMARK OFFICE
CERTIFICATE OF CORRECTION

Page 1 of 2

PATENT NO. : 5,873,851
DATED : February 23, 1999
INVENTOR(S) : I.G. Nilsson

It is certified that error appears in the above-indentified patent and that said Letters Patent is hereby corrected as shown below:

| COLUMN | LINE | | | |
|---|---|---|---|---|
| [56] col. 1 | Refs. Cited (U.S. Patent Docs.) | Please insert the following references: | | |
| | | --4,573,979 | 3/1986 | Blake |
| | | 4,825,865 | 5/1989 | Zelman |
| | | 4,904,238 | 2/1990 | Williams |
| | | 5,123,905 | 6/1992 | Kelman |
| | | 5,139,504 | 8/1992 | Zelman |
| | | 5,217,465 | 6/1993 | Steppe |
| | | 5,242,449 | 9/1993 | Zaleski |
| | | 5,364,405 | 1/1994 | Zaleski-- |
| 6 (Claim 2, | 17 line 1) | "support members" should read --one or more reinforcement members-- | | |
| 6 (Claim 2, | 18-19 lines 2-3) | "extending between" should read --joining-- | | |

UNITED STATES PATENT AND TRADEMARK OFFICE
CERTIFICATE OF CORRECTION

PATENT NO. : 5,873,851
DATED : February 23, 1999
INVENTOR(S) : I.G. Nilsson

It is certified that error appears in the above-indentified patent and that said Letters Patent is hereby corrected as shown below:

| COLUMN | LINE | |
|---|---|---|
| 6 (Claim 3, | 31 line 11) | Before "preventing" delete "for" |

Signed and Sealed this

Twenty-fourth Day of August, 1999

Attest:

Q. TODD DICKINSON

*Attesting Officer*  *Acting Commissioner of Patents and Trademarks*